(12) United States Patent
Pan

(10) Patent No.: US 8,835,490 B2
(45) Date of Patent: *Sep. 16, 2014

(54) METHODS FOR ENHANCING ENERGY METABOLISM

(75) Inventor: Yuanlong Pan, Chesterfield, MO (US)

(73) Assignee: Nestec SA, Vevey (CH)

( * ) Notice: Subject to any disclaimer, the term of this patent is extended or adjusted under 35 U.S.C. 154(b) by 304 days.

This patent is subject to a terminal disclaimer.

(21) Appl. No.: 12/737,721

(22) PCT Filed: Aug. 10, 2009

(86) PCT No.: PCT/US2009/004584
§ 371 (c)(1),
(2), (4) Date: Mar. 18, 2011

(87) PCT Pub. No.: WO2010/019212
PCT Pub. Date: Feb. 18, 2010

(65) Prior Publication Data
US 2011/0165125 A1    Jul. 7, 2011

Related U.S. Application Data

(60) Provisional application No. 61/189,036, filed on Aug. 15, 2008.

(51) Int. Cl.
| | | |
|---|---|---|
| A01N 43/16 | (2006.01) | |
| A61K 31/35 | (2006.01) | |
| C07D 311/00 | (2006.01) | |
| A23K 1/18 | (2006.01) | |
| A23K 1/16 | (2006.01) | |

(52) U.S. Cl.
CPC ............ *A23K 1/1618* (2013.01); *A23K 1/1846* (2013.01)
USPC .......................................... 514/456; 549/403

(58) Field of Classification Search
CPC . A61K 36/87; A61K 31/426; A61K 2300/00; A61K 36/07; A61K 31/192; A61K 31/353; A61K 31/26; A61K 31/05; A61K 31/4439; A61K 31/155; A61K 31/19; A61K 31/194; A61K 31/015; A61K 45/06; A61K 31/198; A23L 1/3051; A23L 2/52
See application file for complete search history.

(56) References Cited

U.S. PATENT DOCUMENTS

| | | | | |
|---|---|---|---|---|
| 5,952,374 A | * | 9/1999 | Clarkson et al. | ............... 514/456 |
| 6,524,616 B1 | * | 2/2003 | Notelivitz et al. | ............. 424/464 |
| 8,193,240 B2 | * | 6/2012 | Pan | ............................... 514/453 |
| 8,226,973 B2 | * | 7/2012 | Pan | ............................... 424/442 |

OTHER PUBLICATIONS (R) Ma et al., Effect of Soy Protein containing Soy Isoflavones on Blood Lipids in Moderately Hypercholesterolemic Adults: A Randomized Controlled Trial, J. Am. College of Nutrition, 24(4), 275-285 (Sep. 2005).*
(S) Davis et al., "Soy Protein Influences Insulin Sensitivity and Cardiovascular Risk in Male Lean SHHF Rats," Hormone and Metabolic Research, 37(5), 309-315 (Jul. 2005).*
(T) Ishihara et al., "A Soybean Peptide Isolate Diet Promotes Postprandial Carbohydrate Oxidation and Energy Expenditure in Type II Diabetic Mice," Journal of Nutrition, 133(3), 752-757 (Mar. 2003).*

* cited by examiner

*Primary Examiner* — Lawrence E Crane
(74) *Attorney, Agent, or Firm* — Ronald A. Burchett; Janet E. Reed

(57) ABSTRACT

The invention provides methods for one or more of enhancing energy metabolism, promoting healthy energy metabolism, maintaining healthy energy metabolism, preventing conditions that result in a decline or deficiency in energy metabolism, treating conditions that result in a decline or deficiency in energy metabolism, and preventing the accumulation of excess body fat in animals without reducing energy intake by the animals. The methods comprise administering isoflavones to the animals, preferably in amounts of from about 0.001 to about 10 g/kg/day.

16 Claims, No Drawings

METHODS FOR ENHANCING ENERGY METABOLISM

CROSS REFERENCE TO RELATED APPLICATIONS

This application is a national stage application under 35 U.S.C. §371 of PCT/US2009/004584 filed Aug. 10, 2009, which claims priority to U.S. Provisional Application Ser. No. 61/189,036 filed Aug. 15, 2008, the disclosures of which are incorporated herein by reference.

BACKGROUND OF THE INVENTION

1. Field of the Invention

The invention relates generally to methods for enhancing energy metabolism and particularly to methods for using isoflavones for enhancing energy metabolism.

2. Description of Related Art

Isoflavones are naturally occurring chemical compounds found in plants such as beans and legumes, particularly soy. Although the mechanism of action is unclear, isoflavones mimic the effects of estrogen and modulate estrogen metabolism. As a result, isoflavones are known to reduce tumor cell proliferation, induce tumor cell apoptosis, regulate hormone balance, and reduce the risks of breast and prostate cancer, heart disease, osteoporosis, and several other diseases and conditions. However, isoflavones are not known to have an affect on energy metabolism.

Energy metabolism is the transformation of energy that accompanies biochemical reactions in the body. Energy metabolism is often reduced or impaired in animals, particularly aging animals, postmenopausal animals, or animals experiencing health or other problems that cause a reduction in energy metabolism. See, Roberts et. al., Nutrition and Aging: Changes in the Regulation of Energy Metabolism With Aging, Physiol. Rev. 86: 651-667, 2006. In such animals, energy expenditure associated with physical activity and basal metabolic rate generally decreases. Such reduced or impaired energy metabolism often results in increased fat deposition and reduced muscle mass. This occurs even though food and energy intake remain the same. This result increases the risk of many chronic diseases such as type II diabetes, hyperlipidemia, arteriosclerosis, and hypertension; lowers the animal's quality of life; and reduces the animal's life-span.

Methods for affecting energy metabolism are known. US20080057584A1 discloses methods for enhancing energy metabolism by introducing nucleic acid that encodes a factor for improving energy metabolism into eukaryotes. WO05107779 discloses compositions for enhancing energy metabolism comprising garcinia cambogia extract, gymnema sylvestre leaf extract, and green tea leaf extract. WO05041949 discloses compositions for affecting dysfunctional energy metabolism comprising a combination of L-carnitine, acetyl-L-carnitine, pantothenate, and niacinamide. U.S. Pat. No. 5,889,055 and U.S. Pat. No. 5,973,004 disclose the use of L-carnitine and acetyl-L-carnitine in combination for the prevention and treatment of syndromes related to diseases of energy metabolism. WO08066250 discloses compositions for enhancing energy metabolism in liver cells comprising chito-oligosaccharides. WO0195915 discloses compositions for enhancing energy metabolism in muscle cells comprising an alkanoyl carnitine and ribose. WO07043933 discloses the use of probiotics for, among other things, improving energy metabolism. U.S. Pat. No. 6,333,421 discloses using capsaicinoide-like compounds for enhancing activity of energy metabolism. However, there have been no effective nutritional solutions to counteract the adverse effects of reduced energy metabolism in animals, particularly aging animals. There is, therefore, a need for novel nutritional solutions that effectively enhance energy metabolism in animals.

SUMMARY OF THE INVENTION

It is, therefore, an object of the invention to provide methods for enhancing energy metabolism in animals.

It is another object of the invention to provide methods for promoting and maintaining healthy energy metabolism in animals.

It is a further object of the invention to provide methods for preventing or treating conditions that result in a decline or deficiency in energy metabolism in animals.

It is another object of the invention to provide methods for preventing the accumulation of excess body fat in animals without reducing energy intake by the animals.

It is another object of the invention to provide methods for promoting the health or wellness of animals.

It is another object of the invention to provide methods for extending the prime years of an animal's life.

One or more of these or other objects are achieved by administering isoflavones to animals in amounts sufficient for enhancing energy metabolism, promoting and maintaining healthy energy metabolism, preventing or treating conditions that result in a decline or deficiency in energy metabolism, or preventing the accumulation of excess body fat in animals without reducing energy intake by the animals. In general embodiments, the isoflavones are administered to the animals in amounts of from about 0.001 to about 10 grams per kilogram of body weight per day (g/kg/day) for as long as there is a need for enhancing energy metabolism, promoting and maintaining healthy energy metabolism, preventing or treating conditions that result in a decline or deficiency in energy metabolism, or preventing the accumulation of excess body fat in animals without reducing energy intake by the animals.

Other and further objects, features, and advantages of the invention will be readily apparent to those skilled in the art.

DETAILED DESCRIPTION OF THE INVENTION

Definitions

The term "isoflavones" means isoflavones and their natural or synthetic analogs, derivatives, precursors, and metabolites useful in the invention, including, but not limited to, isoflavones substituted with one or more lignans or coumestans, e.g., pinoresinol, lariciresinol, secoisolariciresinol, matairesinol, hydroxymatairesinol, syringaresinol, sesamin, enterodiol, enterolactone, and coumestrol.

The term "animal" means any animal that has a need for enhancing energy metabolism, promoting and maintaining healthy energy metabolism, preventing or treating conditions that result in a decline or deficiency in energy metabolism, or preventing the accumulation of excess body fat in animals without reducing energy intake by the animals, including human, avian, bovine, canine, equine, feline, hicrine, lupine, murine, ovine, or porcine animals.

The term "aging" means being of advanced age such that an animal has exceeded 50% of the average lifespan for its particular species and/or breed within a species. For example, if the average lifespan for a given breed of dog is 10 years, then a dog within that breed greater than 5 years old would be considered an "aging" dog.

The term "companion animal" means domesticated animals such as cats, dogs, rabbits, guinea pigs, ferrets, hamsters, mice, gerbils, horses, cows, goats, sheep, donkeys, pigs, and the like.

The term "food composition" means a product or composition that is intended for ingestion by an animal.

The term "dietary supplement" means a product that is intended to be ingested in addition to a normal animal diet. Dietary supplements may be in any form, e.g., solid, liquid, gel, tablet, capsule, powder, and the like. Preferably they are provided in convenient dosage forms, e.g., in sachets. Dietary supplements can be provided in bulk consumer packages such as bulk powders, liquids, gels, or oils. Similarly such supplements can be provided in bulk quantities to be included in other food items such as snacks, treats, supplement bars, beverages, and the like.

The term "regular basis" means that the isoflavones of the invention are administered to the animal on a regular and periodic basis over time. For example, the isoflavones can be administered monthly, weekly, or daily as appropriate for the animal. More frequent administration such as twice or three times daily is preferred in certain embodiments.

The term "healthy energy metabolism" means that energy metabolism occurs in animals at a rate and in a manner either mimics the energy metabolism status of healthy young adult animals or that promotes the good health of an animal, including at a rate and in a manner that utilizes calories and avoids unhealthy weight changes.

The term "health and/or wellness of an animal" means the complete physical, mental, and social well being of the animal, not merely the absence of disease or infirmity.

The term "extending the prime" means extending the number of years an animal lives a healthy life and not just extending the number of years an animal lives, e.g., an animal would be healthy in the prime of its life for a relatively longer time.

The term "in conjunction" means that one or more isoflavones or other compound or other composition of the invention are administered to an animal (1) together in a food composition or (2) separately at the same or different frequency using the same or different administration routes at about the same time or periodically. "Periodically" means that the isoflavones or other compound or other composition is administered on a schedule acceptable for a specific compound or composition. "About the same time" generally means that the isoflavones or other compounds or compositions are administered at the same time or within about 72 hours of each other.

The term "single package" means that the components of a kit are physically associated in or with one or more containers and considered a unit for manufacture, distribution, sale, or use. Containers include, but are not limited to, bags, boxes, cartons, bottles, packages such as shrink wrap packages, stapled or otherwise affixed components, or combinations thereof. A single package may be containers of individual isoflavones and food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain instructions on how to use the kit or safety or technical information about one or more components of a kit.

Ranges are used herein as shorthand to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a supplement", "a method", or "a food" includes a plurality of such "supplements", "methods", or "foods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The methods and compositions and other advances disclosed herein are not limited to particular methodologies, protocols, and reagents because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides methods for enhancing energy metabolism in animals. The methods comprise administering to the animals an energy metabolism enhancing amount of one or more isoflavones.

In another aspect, the invention provides methods for promoting or maintaining healthy energy metabolism in animals. The methods comprise administering to the animals a healthy energy metabolism promoting or maintaining amount of one or more isoflavones.

In another aspect, the invention provides methods for preventing or treating conditions that result in a decline or deficiency in energy metabolism in animals. The methods comprise administering to the animals a condition preventing or treating amount of one or more isoflavones. A condition that results in a decline or deficiency in energy metabolism in animals can be any condition known to skilled artisans, e.g., disease such as hypothyroidism. In various embodiments, the condition is caused by a change in the animal's status, e.g., aging, menopause, andropause, spaying, or neutering. In other embodiments, the conditions are conditions caused by drugs or other compounds that decrease energy metabolism, typically drugs that are administered to a patient for treatment of disease. In further embodiments, the conditions are inherited metabolic disorders that result in a decrease in energy metabolism.

The inventions are based upon the discovery that isoflavones have an affect on energy metabolism and particularly that isoflavones are useful for enhancing energy metabolism in animals, for promoting or maintaining healthy energy metabolism in animals, and for preventing or treating conditions that result in a decline or deficiency in energy metabolism.

In another aspect, the invention provides methods for preventing the accumulation of excess body fat in animals without reducing energy intake by the animals comprising administering to the animals (1) a consistent energy intake suitable for maintaining animal health and (2) one or more isoflavones in amounts sufficient for preventing the accumulation of excess body fat in the animals without reducing energy intake by the animals. Under some conditions, animals, particularly aging animals, tend to accumulate excess body fat even though they consume the same amount of energy they consumed before occurrence of the condition. Then, to avoid accumulating the excess body fat, the animals need to restrict energy intake, generally by consuming less energy in the form of food. This aspect of the invention is based upon the surprising discovery that such animals can reduce the accumulation of excess body fat while continuing to consume the same amount of energy if the animals also consume one or more isoflavones in amounts sufficient to prevent the accumulation of such excess body fat. The condition is any condition that promotes an accumulation of excess body fat, e.g., disease or aging. Preferably, the condition is aging and the animal is an aging animals.

In various embodiments, the methods further comprise administering one or more isoflavones in conjunction with one or more probiotics that are useful for improving or enhancing energy metabolism in animals. Any probiotic useful for improving or enhancing energy metabolism can be used in the combination, including those disclosed in WO07043933 (EP1945235A1). Preferably the probiotics are *Lactobacillus casei*, *Lactobacillus acidophilus*, or *Bifidobacterium lactis*. In preferred embodiments, the isoflavones and probiotics are synergistic. Generally, probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Probiotics bacteria such as *Lactobacilli* or *Bifidobacteria* are believed to positively affect the immune response by improving the intestinal microbial balance leading to enhanced antibody production and phagocytic (devouring or killing) activity of white blood cells. *Bifidobacterium lactis* could be an effective probiotic dietary supplement for enhancing some aspects of cellular immunity in aging animals. Probiotics enhance systemic cellular immune responses and may be useful as a dietary supplement to boost natural immunity in otherwise healthy adults. Probiotics include many types of bacteria but generally are selected from four genera of bacteria: *Lactobacillus acidophillus, Bifidobacteria, Lactococcus,* and *Pediococcus*. Beneficial species include *Enterococcus* and *Saccharomyces* species, e.g., *Enterococcus faecium* SF68. The amount of probiotics to be administered to an animal is determined by the skilled artisan based upon the type and nature of the probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, preferably from about 5 billion to about 10 billion live bacteria per day. The probiotics can be made part of a composition by any suitable means. Generally, the probiotics are mixed with a food composition or applied to the surface of the composition, e.g., by sprinkling or spraying. When the agents are part of a kit, the agents can be admixed with other materials or in their own package.

The animals can be any individual animal of any species or kind, including animals of any age, species, health condition, and the like. In various embodiments, the animals are animals known to experience a decline in energy metabolism, e.g., aging, postmenopausal, postandropausal, spayed, or neutered animals or animals suffering from a condition that causes a decline or deficiency in energy metabolism such as hypothyroidism. In one embodiment, the animal is an aging animal, generally an aging animal that is experiencing a decline in energy metabolism and could therefore benefit from methods for enhancing energy metabolism. In another embodiment, the animal is an animal suffering from a disease that causes a decline in energy metabolism, e.g., a metabolic disorder, inherited metabolic diseases, mitochondrial diseases, and the like.

The isoflavones can be any isoflavones known to skilled artisans. In various embodiments, the isoflavones are selected from the group consisting of isoflavones in the form of aglycons, glucosides, acetyiglucosides, and malonylglucosides. Preferably the isoflavones are selected from the group consisting of biochanin A, daidzein, daidzin, glycitein, formononetin, equol, genistein, irilone, luteone, prunetin, pratensein, and glycitinn. In one embodiment, the isoflavones are soy isoflavones obtained from soy or administered to the animal by feeding soy or soy extracts to the animal. In another embodiment, the isoflavones are isoflavones substituted with one or more lignans or coumestans such as pinoresinol, lariciresinol, secoisolariciresinol, matairesinol, hydroxymatairesinol, syringaresinol, sesamin, enterodiol, enterolactone, and coumestrol.

The isoflavones can be administered to the animals as required to function in the invention, e.g., enhance energy metabolism. Administration amounts can easily be determined by skilled artisans, generally based upon the isoflavone(s) to be administered, the animal, the health conditions and status of the animal, the administration purpose, and the like. The isoflavones are administered as desired or on a regular basis. Preferably, the isoflavones are administered to the animals on a regular basis, preferably on a weekly basis, most preferably in a daily basis. In various embodiments, the isoflavones are administered to the animals in amounts of from about 5 mg/day to about 5000 mg/day, preferably from 10 mg/day to about 2000 mg/day, more preferably from about 30 mg/day to about 500 mg/day, most preferably from about 50 mg/day to about 300 mg/day. In other embodiments, the isoflavones are administered to the animals in amounts of from about 0.001 to about 10 grams per kilogram of body weight per day (g/kg/day), preferably from about 0.05 to about 5 g/kg/day, most preferably from about 0.01 to about 1 g/kg/day. The isoflavones are administered for as long as there is a need for enhancing energy metabolism or for promoting and maintaining healthy energy metabolism. For aging animals, isoflavone administration generally is needed for the remainder of the animal's life.

The isoflavones are administered to the animal in any suitable manner known to skilled artisans. Preferably, the isoflavones are administered to the animal in a composition containing isoflavones, preferably compositions intended for oral administration. In certain embodiments, the isoflavones are administered to the animal as a dietary supplement. In other embodiments, the isoflavones are administered to the animal in a food composition. In one embodiment, a food composition is formulated to provide "complete and balanced" nutrition for an animal, preferably a companion animal, according to standards established by the Association of American Feed Control Officials (AAFCO). In other embodiments, the food compositions are formulated as a companion animal food composition, including a dog or cat food composition. The dietary supplements or food compositions are formulated to contain one or more isoflavones in amounts sufficient to administer the desirable amounts of isoflavones to the animal, i.e., amounts of from about 5 mg to about 5000 mg or amounts sufficient to administer from about 0.001 to about 10 g/kg/day.

In various embodiments, the animal is a human. In others, the animal is a companion animal, preferably a dog or a cat. In some embodiments, the animal is a postmenopausal or postandropausal animal. In others, the animal is a spayed or neutered animal.

In another aspect, the invention provides a package comprising one or more isoflavones and a label affixed to the package containing a word or words, picture, design, acronym, slogan, phrase, or other device, or combination thereof that indicates that the contents of the package contains isoflavones with beneficial properties relating to energy metabolism, e.g., methods for enhancing energy metabolism, promoting healthy energy metabolism, or maintaining healthy energy metabolism. Typically, such device comprises the words "enhances energy metabolism", "promotes healthy energy metabolism", or "maintains healthy energy metabolism", or an equivalent expression printed on the package. Any package or packaging material suitable for containing the composition is useful in the invention, e.g., bag, box, bottle, can, pouch, and the like manufactured from paper, plastic, foil, metal, and the like. In a preferred embodiment, the package contains a food composition adapted for a particular animal such as a human, canine, or feline, as appropriate for the label, preferably a companion animal food composition for dogs or cats. In a preferred embodiment, the package is a can or pouch comprising a food composition of the invention.

In a further aspect, the invention provides a means for communicating information about or instructions for one or more of (1) using isoflavones for enhancing energy metabolism; (2) using isoflavones for promoting healthy energy metabolism; (3) using isoflavones for maintaining healthy energy metabolism; (4) using isoflavones for preventing conditions that result in a decline or deficiency in energy metabolism; (5) using isoflavones for treating conditions that result in a decline or deficiency in energy metabolism; (6) using isoflavones for preventing the accumulation of excess body fat in animals without reducing energy intake by the animals; (7) administering isoflavones for enhancing energy metabolism, promoting healthy energy metabolism, maintaining healthy energy metabolism, preventing conditions that result in a decline or deficiency in energy metabolism, treating conditions that result in a decline or deficiency in energy metabolism, or preventing the accumulation of excess body fat in animals without reducing energy intake by the animals; (8) using isoflavones in conjunction with one or more probiotics that are useful for enhancing energy metabolism in animals; (9) contact information for consumers to use if they have a question the methods and compositions of the invention, e.g., about administering or using isoflavones, food compositions, and probiotics for enhancing energy metabolism, promoting healthy energy metabolism, maintaining healthy energy metabolism, preventing conditions that result in a decline or deficiency in energy metabolism, treating conditions that result in a decline or deficiency in energy metabolism, or preventing the accumulation of excess body fat in animals without reducing energy intake by the animals; and (10) nutritional information about isoflavones. Useful instructions can include administration amounts and frequency for isoflavones. The communication means is useful for instructing on the benefits of using the invention and communicating the approved methods for administering the isoflavones and food compositions containing isoflavones to an animal. The means comprises one or more of a physical or electronic document, digital storage media, optical storage media, audio presentation, audiovisual display, or visual display containing the information or instructions. Preferably, the means is selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In a further aspect, the invention provides kits suitable for administering isoflavones to animals. The kits comprise in separate containers in a single package or in separate containers in a virtual package, as appropriate for the kit component, one or more isoflavones and at least one of (1) one or more ingredients suitable for consumption by an animal; (2) instructions for how to combine isoflavones and other kit components to produce a composition useful for enhancing energy metabolism, promoting and maintaining healthy energy metabolism, preventing or treating conditions that result in a decline or deficiency in energy metabolism, or preventing the accumulation of excess body fat in animals without reducing energy intake by the animals (particularly kit components that are ingredients suitable for consumption by an animal to produce a food composition); (3) instructions for how to use isoflavones for enhancing energy metabolism; (4) instructions for how to use isoflavones for promoting and maintaining healthy energy metabolism; (5) instructions for how to use isoflavones for preventing or treating conditions that result in a decline or deficiency in energy metabolism; (6) instructions for how to use isoflavones for preventing the accumulation of excess body fat in animals without reducing energy intake by the animals; (7) a device for preparing or combining the kit components to produce a composition suitable for administration to an animal such as a spoon or other application device; (8) one or more probiotics that are useful for enhancing energy metabolism in animals; and (9) a device for administering the combined or prepared kit components to an animal such as a bowl or other container.

When the kit comprises a virtual package, the kit is limited to instructions in a virtual environment in combination with one or more physical kit components. The kit contains isoflavones and other components in amounts sufficient for enhancing energy metabolism, for promoting and maintaining healthy energy metabolism, or for preventing the accumulation of excess body fat in animals without reducing energy intake by the animals. Typically, isoflavones and the other suitable kit components are admixed just prior to consumption by an animal. The kits may contain the kit components in any of various combinations and/or mixtures. In one embodiment, the kit contains a packet containing one or more isoflavones and a container of food for consumption by an animal. The kit may contain additional items such as a device for mixing isoflavones and ingredients or a device for containing the admixture, e.g., a food bowl. In another embodiment, isoflavones are mixed with additional nutritional supplements such as vitamins and minerals that promote good health in an animal. The components are each provided in separate containers in a single package or in mixtures of various components in different packages. In preferred embodiments, the kits comprise isoflavones and one or more other ingredients suitable for consumption by an animal. Preferably such kits comprise instructions describing how to combine isoflavones with the other ingredients to form a food composition for consumption by the animal, generally by mixing isoflavones with the other ingredients or by applying isoflavones to the other ingredients, e.g., by sprinkling isoflavones on a food composition.

In one aspect, the invention provides methods for promoting the health or wellness of an animal. The methods comprise administering to the animal a health or wellness promoting amount of one or more isoflavones. The isoflavones promote and maintain healthy energy metabolism in animals and prevent or treat conditions that result in a decline or deficiency in energy metabolism in animals. The methods are useful for promoting the health or wellness of animals of any age or classification, including senior animals, geriatric animals, obese animals, overweight animals, and animals determined to be susceptible to or suffering from conditions that cause a decline or deficiency in energy metabolism in animals. The amount of isoflavones administered to the animal are the same amounts described herein for promoting and maintaining healthy energy metabolism and preventing or treating conditions that result in a decline or deficiency in energy metabolism in animals, e.g., from about 5 mg to about 5000 mg.

In another aspect, the invention provides methods for extending the prime years of an animal's life. The methods comprise administering one or more isoflavones to the animals in an amount effective for extending the prime for the animal. The isoflavones promote and maintain healthy energy metabolism in animals and prevent or treat conditions that result in a decline or deficiency in energy metabolism in animals. As a result, the animals live a healthy life throughout their life, including during the prime years of life. The amount of isoflavones administered to the animal are the same amounts described herein for promoting and maintaining healthy energy metabolism and preventing or treating conditions that result in a decline or deficiency in energy metabolism in animals, e.g., from about 5 mg to about 5000 mg.

In a further aspect, the invention provides for the use of one or more isoflavones to prepare a medicament. In another aspect, the invention provides for the use of isoflavones to prepare a medicament for one or more of enhancing energy metabolism, promoting healthy energy metabolism, maintaining healthy energy metabolism, preventing conditions that result in a decline or deficiency in energy metabolism, treating conditions that result in a decline or deficiency in energy metabolism, and preventing the accumulation of excess body fat in animals without reducing energy intake by the animals. Similarly, the medicaments are useful for promoting the health or wellness of animals and for extending the prime years of an animal's life. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

EXAMPLES

The invention can be further illustrated by the following examples, although it will be understood that these examples are included merely for purposes of illustration and are not intended to limit the scope of the invention unless otherwise specifically indicated.

Example 1

Thirty (30) adult Labrador Retrievers (50% males and 50% females) with a body condition score of 4 to 5 and between the ages of 2 and 3 years old were housed either individually or in groups of 2 dogs per group. The animals fed individually.

Pretest maintenance energy requirement (MER) estimate and randomization during a period of 6 to 12 weeks: To determine the MER for each dog, a chicken & rice complete and balanced dog food was the only diet for all dogs. The initial amount of diet fed to each dog was the average of its food intake for a period of about 4 months. The amount of daily diet was adjusted weekly as needed to maintain a dog's body weight. The diet was placed in a container on the floor for 60 minutes. The diet left was weighed and daily food intake was recorded during the pretest period. The body weight of each dog was monitored weekly. The body weight did not change more than 10% during the last three weeks of pre-test period.

Randomization: After the MER for each dog was determined, the dogs were randomized into two groups (control and isoflavone) with 15 dogs per group based on MER, body weight, percentage of body fat, and gender.

Feeding procedures: The dogs were fed 25% more than their MER for 9 months. The amount of daily food was divided into two equal portions. One was fed in the morning and the other in the afternoon. Dogs had 60 minutes to eat each time. If a dog did not eat all the food within 60 minutes, the food was in the room overnight to make sure that the dog ate 25% more than its MER.

Test Diets: Both the control and isoflavone diets had same levels of protein (29%), fat (18%) and CHO (46%). The isoflavone diet contained 310 mg/kg total isoflavones from soy germ meal.

Measurements: The following measurements were taken: (1) Food intake was collected daily; (2) Body weight was recorded at the baseline, weekly, and at the end of the study; (3) DEXA data (body fat, lean body mass) were collected at the baseline, every 3 months after the initiation of the 9-additional-month treatments, and at the end of the study; and (4) Total energy expenditure was determined at the end of the study by doubly-labeled water (DLW) technique (Am J Clin Nutr 1987; 45:905-913). The DLW method yields an average energy expenditure (EE) for a period of 5 to 14 days. The procedure is noninvasive, nonrestrictive and reflective of actual EE under free-living conditions. Briefly, the DLW method involves enrichment of body water with the stable (natural and nonradioactive) isotopes, deuterium ($2H$) and oxygen-18 ($18O$), and then determination of their monoexponential washout kinetics in plasma. The DLW method is based on the principle that the disappearance rate of 2H reflects water turnover rate whereas the disappearance rate of 18O reflects both water and $CO_2$ turnover rates. Therefore, with time, the difference between the disappearance rates of 2H and 18O represent the rate of $CO_2$ production. Knowing the respiratory quotient (RQ) or food quotient (FQ), EE can be calculated from the $CO_2$ production rates. The data is shown in Table 1.

Referring to Table 1, the data show that isoflavones are useful for enhancing energy metabolism, promoting healthy energy metabolism, or maintaining healthy energy metabolism. There was no significant difference in baseline maintenance energy requirement (MER, expressed as grams of food required to maintain a stable body weight) between control and isoflavone groups. The dogs in the isoflavone groups had significantly (p=0.0481) higher total energy expenditure than the dogs in the control group.

TABLE 1

| Group | Baseline Daily MERs (g ± SEM) | Daily Food Intake (g ± SEM) | Total Daily Energy Expenditure (Kcal/kg body weight/day) |
|---|---|---|---|
| Control | 465.60 ± 27.70 | 582.00 ± 34.76 | 39.41 ± 4.66 |
| Isoflavone | 429.25 ± 26.19 | 536.56 ± 32.74 | 44.58 ± 5.33 |
| p value | 0.3818 | 0.3818 | 0.0481 |

Compared with the control dogs, the isoflavone diet significantly reduced the % body fat gain at 3 (p=0.0483) and 9 months (p=0.0255) after the initiation of the feeding trial. Dogs in the isoflavone group tended to have lower increase in % body fat at 6 months (p=0.106) after the initiation of the feeding trial. The data is shown in Table 2.

TABLE 2

| Group | 3-month (%) | 6-month (%) | 9-month (%) |
|---|---|---|---|
| Control | 5.60 ± 0.92 | 8.31 ± 1.04 | 14.30 ± 1.56 |
| Isoflavone | 3.03 ± 0.80 | 5.96 ± 0.94 | 9.41 ± 1.33 |
| p value | 0.0483 | 0.106 | 0.0255 |

At the end of the 9-month study, dogs fed the isoflavone diet gained significantly less body fat than the control dogs, even though dogs in both groups had the same food intake during the study. The reduced gain in body fat in the isoflavone dogs is due to the enhanced energy metabolism and resulting increased total energy expenditure induced by isoflavones. These data show that isoflavones are effective in promoting and maintaining a healthy energy metabolism in animals and for preventing the accumulation of excess body fat in animals without reducing energy intake by the animals.

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A method for enhancing energy metabolism in a canine in need thereof, comprising identifying a healthy canine for whom enhancement of energy metabolism is needed or desired, and administering to the canine an energy metabolism enhancing amount of a composition comprising soy isoflavones.

2. The method of claim 1 wherein the isoflavones are selected from the group consisting of isoflavones in the form of aglycones, glucosides, acetylglucosides, and malonylglucosides.

3. The method of claim 1 wherein the isoflavones are administered to the canine in amounts of from about 5 mg to about 5000 mg.

4. The method of claim 1 wherein the isoflavones are administered to the canine on a regular basis.

5. The method of claim 4 wherein the isoflavones are administered to the canine in amounts of from about 0.001 to about 10 g/kg/day.

6. The method of claim 1 wherein the canine is an aging canine.

7. The method of claim 1 wherein the canine is postmenopausal or postandropausal.

8. The method of claim 1, further comprising that the composition is a dietary supplement.

9. The method of claim 1, further comprising that the composition is a food composition.

10. The method of claim 9, further comprising that the food composition is formulated to provide complete and balanced nutrition for the canine.

11. The method of claim 1 wherein the canine is spayed or neutered.

12. The method of claim 10 wherein the canine is an aging canine.

13. The method of claim 10 wherein the canine is postmenopausal or postandropausal.

14. The method of claim 10 wherein the canine is spayed or neutered.

15. The method of claim 1 further comprising administering the composition in conjunction with probiotic microorganisms.

16. A method for promoting or maintaining healthy energy metabolism in a canine in need thereof, comprising identifying a healthy canine for whom promoting or maintaining healthy energy metabolism is needed or desired, and administering to the canine a healthy energy metabolism promoting or maintaining amount of soy isoflavones.

* * * * *